US012620492B2

(12) United States Patent
Oh et al.

(10) Patent No.: US 12,620,492 B2
(45) Date of Patent: May 5, 2026

(54) ACUTE STRESSORS DETECTION FOR RECOGNIZING MALADAPTATION IN PHYSIOLOGICAL CONDITIONS

(71) Applicants:Zepp, Inc., Cupertino, CA (US); Anhui Huami Health Technology Co., Ltd., Hefei (CN)

(72) Inventors: Hyungik Oh, Cupertino, CA (US); Mengfan Tang, Cupertino, CA (US); Kongqiao Wang, Hefei (CN)

(73) Assignees: Zepp, Inc., Milpitas, CA (US); Anhui Huami Health Technology Co., Ltd., Hefei (CN)

( * ) Notice: Subject to any disclaimer, the term of this patent is extended or adjusted under 35 U.S.C. 154(b) by 558 days.

(21) Appl. No.: 17/994,921

(22) Filed: Nov. 28, 2022

(65) Prior Publication Data

US 2024/0177864 A1 May 30, 2024

(51) Int. Cl.
*G16H 50/30* (2018.01)
*A61B 5/00* (2006.01)
(Continued)

(52) U.S. Cl.
CPC ......... *G16H 50/30* (2018.01); *A61B 5/02405* (2013.01); *A61B 5/165* (2013.01); *A61B 5/7282* (2013.01)

(58) Field of Classification Search
CPC .... G16H 50/30; G16H 50/20; A61B 5/02405; A61B 5/7275
See application file for complete search history.

(56) References Cited

U.S. PATENT DOCUMENTS

| | | | |
|---|---|---|---|
| 10,321,829 B2 | 6/2019 | Colley et al. | |
| 2008/0214904 A1* | 9/2008 | Saeed .................. | A61B 5/0006 |
| | | | 705/2 |

(Continued)

FOREIGN PATENT DOCUMENTS

| | | | |
|---|---|---|---|
| CN | 112040838 A | 12/2020 | |
| CN | 113646027 A | 11/2021 | |
| WO | WO-2017217597 A1 * | 12/2017 | ........... A61B 5/0006 |

OTHER PUBLICATIONS

Ahmad S, Ramsay T, Huebsch L, Flanagan S, McDiarmid S, Batkin I, McIntyre L, Sundaresan SR, Maziak DE, Shamji FM, Hebert P, Fergusson D, Tinmouth A, Seely AJ. Continuous multi-parameter heart rate variability analysis heralds onset of sepsis in adults. PLoS One. Aug. 14, 2009;4(8):e6642. (Year: 2009).*

(Continued)

*Primary Examiner* — Evangeline Barr
(74) *Attorney, Agent, or Firm* — Young Basile Hanlon & MacFarlane, P.C.

(57) ABSTRACT

A method of acute stressors detection includes obtaining, by a processor, heart rate variability (HRV) data determined based on an HRV-related metric associated with an individual; determining, based on the HRV data, whether an HRV event indicative of a maladaptation risk of the individual has occurred; and responsive to determining that the HRV event indicative of the maladaptation risk of the individual has occurred, using a causal inference engine to determine at least one acute stressor as a probable cause of the HRV event based on inputs comprising the HRV event and lifestyle data associated with the individual, wherein the lifestyle data comprises at least one lifestyle event and environmental contexts associated with the at least one lifestyle event performed by the individual.

20 Claims, 6 Drawing Sheets

(51) Int. Cl.
  *A61B 5/024* (2006.01)
  *A61B 5/16* (2006.01)

(56) References Cited

U.S. PATENT DOCUMENTS

| | | | | |
|---|---|---|---|---|
| 2017/0216672 | A1* | 8/2017 | Wisbey | H04R 1/1041 |
| 2022/0015695 | A1* | 1/2022 | Margarito | A61B 5/4809 |
| 2022/0296100 | A1* | 9/2022 | Gargaro | A61B 5/02 |
| 2023/0317279 | A1* | 10/2023 | Hasan | G16H 50/20 |
| | | | | 705/3 |

OTHER PUBLICATIONS

Pearl, Judea,; Causal inference in statistics: An overview; Statistics surveys 3 (2009): 96-146.

Plews, Daniel J., et al.; Training adaptation and heart rate variability in elite endurance athletes: opening the door to effective monitoring; Sports medicine 43.9 (2013): 773-781.

https://headsuphealth.com/blog/features/tracking-the-oura-hrv-coefficient-of-variation-hrv-cv.

https://medium.com/@altini_marco/building-hrv4training-pro-97c9a9d1b37d.

https://elitehrv.com/improving-hrv-data-interpretation-coefficient-variation.

Kiviniemi, AM, Hautala AJ, Kinnuen H, Tulppo MP; Endurance training guided individually by daily heart rate variability measurements. European journal of applied physiology. 007;101(6):743-751.

https://www.hrv4training.com.

https://www.garmin.com/en-US/garmin-technology/health-science/body-battery.

https://www.whoop.com/experience/#:~:text=WHOOP%20Recovery%20quantifies%20your%20readiness,recovery%20day%20or%20requires%20rest.

https://www.fitbit.com/global/us/technology/stress.

https://www.garmin.com/en-US/garmin-technology/health-science/stress-tracking.

https://www.samsung.com/us/support/answer/ANS00080574.

Aeschbacher, Stefanie, et al.; Healthy lifestyle and heart rate variability in young adults. European journal of preventive cardiology 23.10 (2016): 1037-1044.

Reginato, Elena, et al.; Dietary and lifestyle patterns are associated with heart rate variability. Journal of clinical medicine 9.4 (2020): 1121.

Felber Dietrich, Denise, et al.; Heart rate variability in an ageing population and its association with lifestyle and cardiovascular risk factors: results of the SAPALDIA study. Europace 8.7 (2006): 521-529.

Clawson, J., Pater, J. A., Miller, A. D., Mynatt, E. D., and Mamykina, L. No longer wearing: investigating the abandonment of personal health-tracking technologies on craigslist. In Proceedings of the 2015 ACM International Joint Conference on Pervasive and Ubiquitous Computing, ACM (2015), 647-658.

Cordeiro, F., Epstein, D. A., Thomaz, E., Bales, E.,Jagannathan, A. K., Abowd, G. D., and Fogarty, J. Barriers and negative nudges: Exploring challenges in food journaling. In Proceedings of the 33rd Annual ACM Conference on Human Factors in Computing Systems, ACM (2015), 1159-1162.

Epstein, D. A., Ping, A., Fogarty, J., and Munson, S. A.; A lived informatics model of personal informatics. In Proceedings of the 2015 ACM International Joint Conference on Pervasive and Ubiquitous Computing, ACM (2015), 731-742.

Lazar, A., Koehler, C., Tanenbaum, J., and Nguyen,D. H.; Why we use and abandon smart devices. In Proceedings of the 2015 ACM International Joint Conference on Pervasive and Ubiquitous Computing, ACM (2015), 635-646.

https://www.firstbeat.com/en/blog/real-time-trimp-min/#:~:text=What%20is%20TRIMP%3F,represented%20by%20a%20single%20number.

https://medium.com/@altini_marco/the-ultimate-guide-to-heart-rate-variability-hrv-part-2-323a38213fbc.

Altini, Marco, and Daniel Plews; What is behind changes in resting heart rate and heart rate variability? A large-scale analysis of longitudinal measurements acquired in free-living. Sensors 21.23 (2021): 7932.

https://www.hrv4training.com/blog/daily-score-baseline-and-normal-range-an-overview.

https://www.hrv4training.com/blog/the-big-picture.

https://www.hrv4training.com/blog/coefficient-of-variation-cv-what-is-it-and-how-can-you-use-it.

https://www.hrv4training.com/blog/acute-changes-in-heart-rate-variability.

https://www.hrv4training.com/blog/interpreting-hrv-trends.

https://www.hrv4training.com/blog/redefining-hrv4trainings-daily-advice.

https://www.hrv4training.com/blog/heart-rate-variability-hrv-in-team-sports.

* cited by examiner

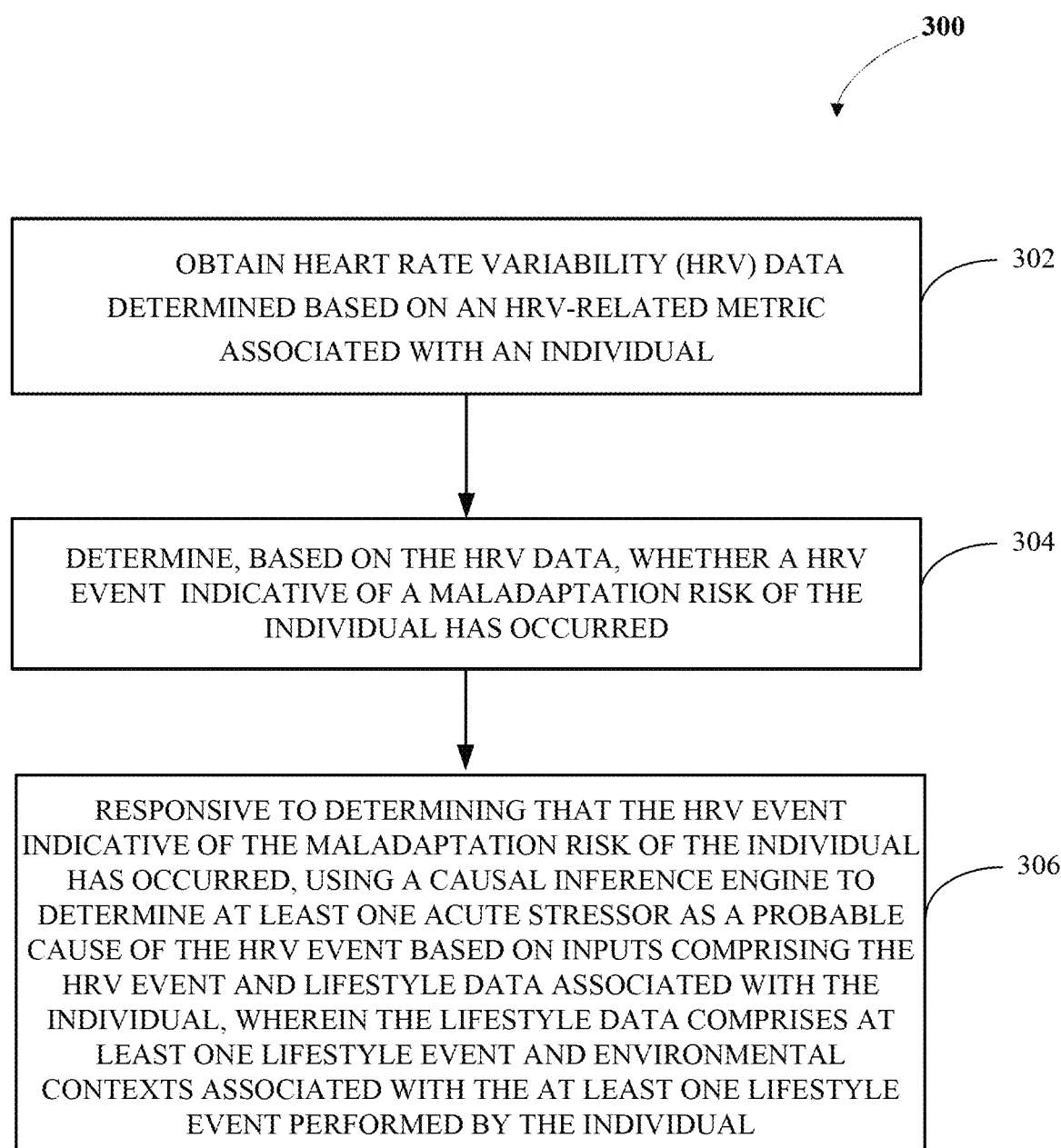

300

OBTAIN HEART RATE VARIABILITY (HRV) DATA
DETERMINED BASED ON AN HRV-RELATED METRIC
ASSOCIATED WITH AN INDIVIDUAL

302

DETERMINE, BASED ON THE HRV DATA, WHETHER A HRV
EVENT INDICATIVE OF A MALADAPTATION RISK OF THE
INDIVIDUAL HAS OCCURRED

304

RESPONSIVE TO DETERMINING THAT THE HRV EVENT
INDICATIVE OF THE MALADAPTATION RISK OF THE INDIVIDUAL
HAS OCCURRED, USING A CAUSAL INFERENCE ENGINE TO
DETERMINE AT LEAST ONE ACUTE STRESSOR AS A PROBABLE
CAUSE OF THE HRV EVENT BASED ON INPUTS COMPRISING THE
HRV EVENT AND LIFESTYLE DATA ASSOCIATED WITH THE
INDIVIDUAL, WHEREIN THE LIFESTYLE DATA COMPRISES AT
LEAST ONE LIFESTYLE EVENT AND ENVIRONMENTAL
CONTEXTS ASSOCIATED WITH THE AT LEAST ONE LIFESTYLE
EVENT PERFORMED BY THE INDIVIDUAL

ACUTE STRESSORS DETECTION FOR RECOGNIZING MALADAPTATION IN PHYSIOLOGICAL CONDITIONS

FIELD

The present disclosure relates generally to physical health care monitoring, and more specifically, to acute stressors detection.

BACKGROUND

With modern technologies, we have the ability to sense and compute upon health-related data ubiquitously and continuously, and apply this information towards improved health. A serious challenge remains in transforming this collected data to real-world improvements in individual health. Furthermore, delivering better health quality to people without excessive cost is also key to allow societal resources to go towards progress in other domains.

SUMMARY

Disclosed herein are implementations of methods, apparatuses, and systems for acute stressors detection.

In one aspect, a method of acute stressors detection is disclosed. The method includes obtaining, by a processor, heart rate variability (HRV) data determined based on an HRV-related metric associated with an individual; determining, based on the HRV data, whether an HRV event indicative of a maladaptation risk of the individual has occurred; and responsive to determining that the HRV event indicative of the maladaptation risk of the individual has occurred, using a causal inference engine to determine at least one acute stressor as a probable cause of the HRV event based on inputs comprising the HRV event and lifestyle data associated with the individual, wherein the lifestyle data comprises at least one lifestyle event and environmental contexts associated with the at least one lifestyle event performed by the individual.

In another aspect, an apparatus for acute stressors detection is disclosed. The apparatus includes a non-transitory memory; and a processor, wherein the non-transitory memory includes instructions executable by the processor to: obtain, by a processor, heart rate variability (HRV) data determined based on an HRV-related metric associated with an individual, the HRV data comprising an HRV baseline; determine, based on the HRV data, whether an HRV event indicative of a maladaptation risk of the individual has occurred; and responsive to determining that the HRV event indicative of the maladaptation risk of the individual has occurred, use a causal inference engine to determine at least one acute stressor as a probable cause of the HRV event based on inputs comprising the HRV event and lifestyle data associated with the individual, wherein the lifestyle data comprises at least one lifestyle event and environmental contexts associated with the at least one lifestyle event performed by the individual.

In another aspect, a non-transitory computer-readable storage medium configured to store computer programs for acute stressors detection is disclosed. The computer programs include instructions executable by a processor to: obtain, by a processor, heart rate variability (HRV) data determined based on an HRV-related metric associated with an individual; determine, based on the HRV data, whether an HRV event indicative of a maladaptation risk of the individual has occurred; and responsive to determining that the HRV event indicative of the maladaptation risk of the individual has occurred, use a causal inference engine to determine at least one acute stressor as a probable cause of the HRV event based on inputs comprising the HRV event and lifestyle data associated with the individual, wherein the lifestyle data comprises at least one lifestyle event and environmental contexts associated with the at least one lifestyle event performed by the individual.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 3 is a flowchart of an example process of acute stressors detection according to some implementations of this disclosure.

DETAILED DESCRIPTION

Figure 1:
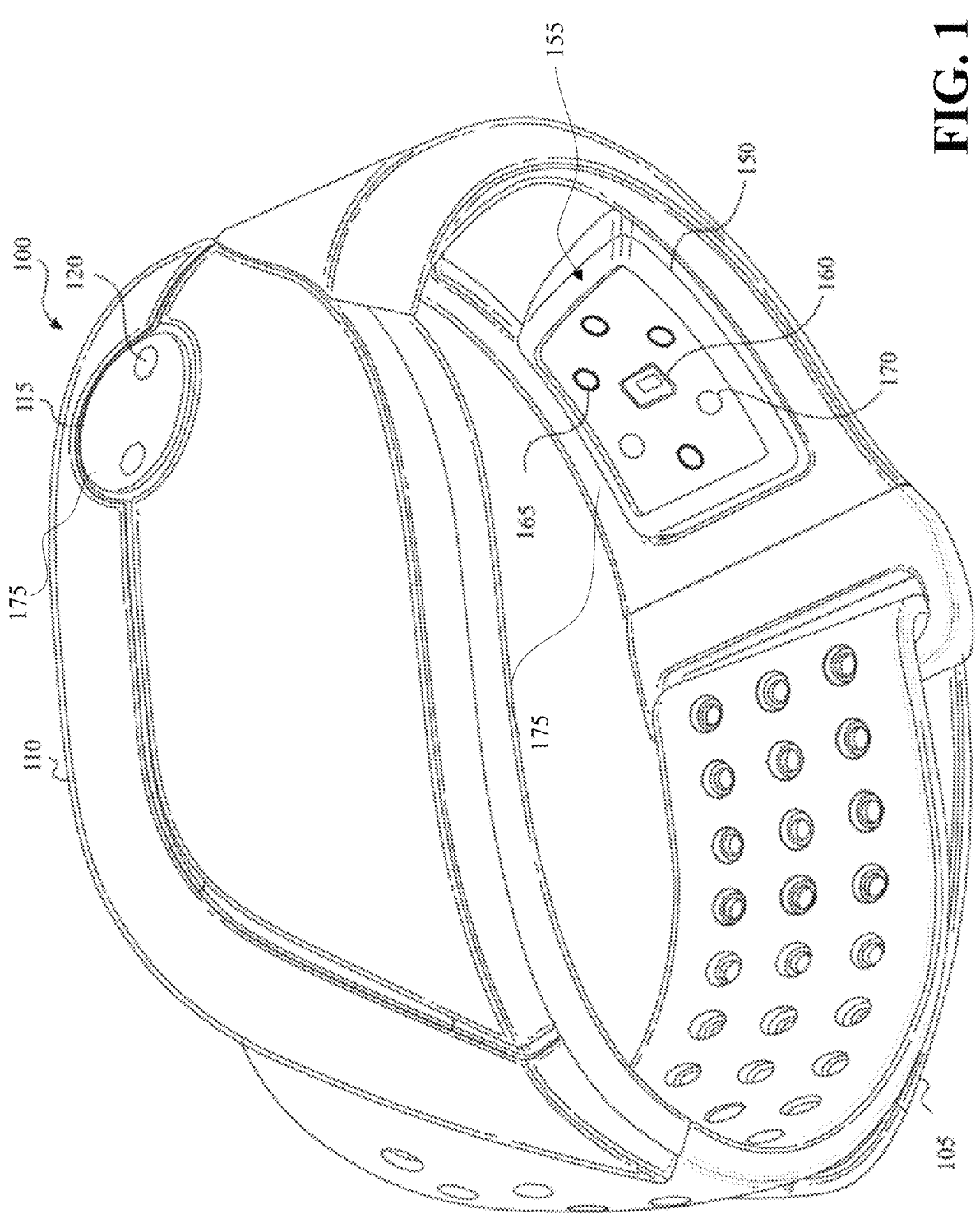
FIG. 1 depicts a perspective view of an example wearable device according to some implementations of this disclosure.

Many portable devices and systems have been developed to monitor physiological conditions of an individual. One area of interest in the use of physiological monitors is personal wellness and physical exercise for purposes of fitness training, weight loss, or monitoring general health. This can include monitoring of heart rate, glucose level, apnea, respiratory stress, and other physiological conditions. For example, physiological parameters of the individual can be continuously tested, including periodic recording of heart rate variability, to assess stress level and physical fitness of the individual. The assessment may be carried out automatically during the individual's daily physical activities. Based on the assessment, various actions can be taken to keep the individual's health state.

In some instances, physiological conditions of the individual can be monitored by, for example, displaying scores, such as stress level, body battery, or recovery score, which gives the individual insights regarding their current physiological states.

Using a data-driven approach, data from wearable devices such as smart watches can be analyzed to reveal what lifestyle pattern could negatively affect an individual's physiology, implementations of this disclosure aim to help the individual to reduce physiological stress. For example, heart rate variability (HRV) data, which relates to physiological measure of fluctuations of time intervals between heartbeats, can provide indications about the overall physical health of a person.

According to implementations of this disclosure, a causal inference method is used to detect acute stressor(s) for an individual. The acute stressors represent inputs that affects the individual's physiology in the immediate future, for example, such as lower than normal sleep duration, higher than normal workout, or decreasing sleep duration during consecutive days, etc. The acute stressors can be based on lifestyle events of the individual. Based on the HRV data and lifestyle data for the individual, the acute stressor(s) can be detected, for example, using a causal inference engine, e.g., using a casual interference technique based on conditional probability.

By linking the HRV data to the individual's lifestyle data and finding the reason why the individual's physiological condition (e.g., daily HRV score) becomes bad can be determined by figuring out the causal relationship between the HRV data and the individual's lifestyle events. According to implementations of this disclosure, risky HRV trends that require more attention can be determined; life events and their contexts can be extracted from collected sensor data (e.g., from a smart watch) and used to build a causal model; and the most likely evidence that could have caused the risky HRV trends can be determined using the casual model.

According to implementations of this disclosure, sensor data for the individual can be collected, for example, by wearable devices. The collected sensor data for the individual can be extracted to obtain the HRV data and the lifestyle data. The lifestyle events and corresponding environmental contexts can be extracted from the lifestyle data. Based on one or more rules, the HRV data (e.g., daily HRV score, HRV trend data etc.) can be used to determine whether the HRV event indicative of a maladaptation risk of the individual has occurred. When the HRV event indicative of the maladaptation risk of the individual is determined to have occurred, the causal inference engine can use, in some implementations, a directed acyclic graph based on probability theory (e.g., Bayes method) to determine at least one acute stressor based on inputs including the HRV event, the lifestyle events, and corresponding environmental contexts. The at least one acute stressor can be a probable cause of the HRV event. The at least one acute stressor can be notified to the individual to inform the individual to take actions to reduce activities that cause the at least one acute stressor.

It should be noted that the applications and implementations of this disclosure are not limited to the examples, and alternations, variations, or modifications of the implementations of this disclosure can be achieved for any computation environment. Details of the disclosed methods, apparatus, and systems will be set forth below after an overview of the system and coding structures.

FIG. 1 depicts a perspective view of an example device 100 according to some implementations of this disclosure. The device 100 may be a physiological monitor worn by an individual (also referred to herein as a user) to at least one of sense, collect, monitor, analyze, or display information pertaining to one or more physiological characteristics to provide physiological information. The device 100 can include, for example, a band, a ring, a strap (e.g., a chest strap), or wristwatch. According to FIG. 1, the device 100 can include a wearable monitoring device configured for positioning at a user's wrist, arm, finger, chest, another extremity of the user, or some other area of the user's body.

The device 100 may include at least one of an upper module 110 or a lower module 150, each including at least one of one or more sensing tools including sensors and processing tools for detecting, collecting, processing, or displaying one or more physiological parameters and/or physiological characteristics of a user and/or other information that may or may not be related to health, wellness, exercise, sleep, or physical training sessions (e.g., characteristic information).

The upper module 110 and the lower module 150 of the device 100 may include a strap or band 105 extending from opposite edges of each module for securing device 100 to the user. The band(s) 105 may include an elastomeric material or the band(s) 105 may include some other suitable material, including but not limited to, a fabric or metal material.

Upper module 110 or lower module 150 may also include a display unit (not shown) for communicating information to the user (i.e., the wearer of the device). The display unit may be an LED indicator including a plurality of LEDs, each a different color. The LED indicator can be configured to illuminate in different colors depending on the information being conveyed. For example, where device 100 is configured to monitor at the user's heart rate, the display unit may illuminate light of a first color when the user's hear rate is in a first numerical range, illuminate light of a second color when the user's hear rate is in a second numerical range, and illuminate light of a third color when the user's hear rate is in a third numerical range. In this manner, a user may be able to detect his or her approximate heart rate at a glance, even when numerical heart rate information is not displayed at the display unit, and/or the user only sees device 100 through the user's peripheral vision.

The display unit may include a display screen for displaying images, characters, graphs, waveforms, or a combination thereof to at least one of the user or a medical professional. The display unit may further include one or more hard or soft buttons or switches configured to accept input by the user. The display unit may switch or be toggled between displaying user physiological information.

The device 100 may further include one or more communication modules. Each of the upper module 110 and the lower module 150 may include a communication module such that information received at either module can be shared with the other module. One or more communication modules may also communicate with other devices such as personal device of the user (such as a handheld device, a smart phone, a tablet, a laptop computer, a desktop computer, or the like) or a server (such as a cloud-based server). The communications between the upper and lower modules can be transmitted from one module to the other wirelessly (e.g., via Bluetooth, RF signal, Wi-Fi, near field communications, etc.) or through one or more electrical connections embedded in band 105. Any analog information collected or analyzed by either module can be translated to digital information for reducing the size of information transfers between modules. Similarly, communications between either module and device can be transmitted wirelessly or through a wired connection, and translated from analog to digital information to reduce the size of data transmissions.

As shown in FIG. 1, lower module 150 can include an array of sensor array 155 including but not limited to one or more optical detectors 160, one or more light sources 165, one or more contact pressure/tonometry sensors 170, and at least one of the one or more gyroscopes or accelerometers 175. These sensors are only illustrative of the possibilities, however, and lower module may include additional or alternative sensors such as one or more acoustic sensors, electromagnetic sensors, ECG electrodes, bio impedance sensors, or galvanic skin response, or a combination thereof. Though not depicted in the view shown in FIG. 1, upper module 110 may also include one or more such sensors and components on its inside surface, i.e., the surface in contact with the user's tissue or targeted area.

The location of sensor array 155 or the location of one or more sensor components of sensor array 155 with respect to the user's tissue may be customized to account for differences in body type across a group of users or placement in different locations on a user. For example, band 105 may include an aperture or channel within which lower module 150 is movably retained. In one implementation, lower module 150 and channel can be configured to allow lower module 150 to slide along the length of channel using, for example, a ridge and groove interface between the two components. For example, if the user desires to place one or more components of sensor array 155 at a particular location on his or her wrist, or mid-section, the lower module 150 can be slid into the desired location along band 105. Though not depicted in FIG. 1, band 105 and upper module 110 can be similarly configured to allow for flexible or customized placement of one or more sensor components of upper module 110 with respect to the user's wrist or targeted tissue area.

The sensors and components proximate or in contact with the at least one of the user's tissue, upper module 110, or lower module 150 may include additional sensors or components on their respective outer surfaces, i.e., the surfaces facing outward or away from the user's tissue. In the implementation depicted in FIG. 1, upper module 110 includes one such outward facing sensor array 115. The sensor array 115 may include one or more ECG electrodes 120, and/or one or more gyroscopes and/or accelerometers 175. Similar to the sensor arrays of the upper and lower modules proximate or in contact with the user's tissue, outward facing sensor array 115 may further include one or more contact pressure/tonometry sensors, photo detectors, light sources, acoustic sensors, electromagnetic sensors, bio impedance sensors, accelerometer, gyroscope, and/or galvanic skin response sensors.

The outward facing sensors of sensor array 115 can be configured for activation when touched by the user (with his or her other hand) and used to collect additional information. The outward facing sensors may measure without being in direct contact with the user. The outward facing sensors of sensor array 115 may be an accelerometer 175 and the accelerometer 175 may indirectly monitor movements or micro-movements (e.g., an acceleration or a velocity change) that are transmitted to the sensor through the band or the module moving or being moved or a gyroscope that monitors velocities to determine micro-movements. In an example, where lower module 150 includes one or more optical detectors 160 and light sources 165 for collecting ECG, PPG, or heart rate information of the user, outward facing sensor array 115 of upper module 110 may include ECG electrodes 120 that can be activated when the user places a fingertip in contact with the electrodes. While the optical detectors 160 and light sources 165 of lower module 150 can be used to continuously monitor blood flow of the user, outward facing sensor array 115 of upper module 110 can be used periodically or intermittently to collect potentially more accurate blood flow information which can be used to supplement or calibrate the measurements collected and analyzed by an inward facing sensor array, the sensor array 155, of lower module 150.

In addition to the inward and outward facing sensors, device 100 may further include additional internal components such at least one of the as one or more accelerometers or gyroscopic components for determining whether and to what extent the user is in motion (i.e., whether the user is walking, jogging, running, swimming, sitting, or sleeping), breathing rhythm, breathing signals, or a combination thereof of a user. Information collected by at least one of the accelerometer(s) or gyroscopic components can also be used to calculate the number of steps a user has taken over a period of time. The activity information may measure movements. The movements measured may be macro-movements such as walking or jogging. The movements may be micro-movements.

The micro-movements may be caused by a surface of a user's skin or body part being moved due to, for example, respiration, heartbeat, or a combination thereof. The micro-movements may have a displacement (e.g., length) less than a predetermined displacement in order for at least one of the accelerometer or gyroscope to at least one of the measure or record the micro-movements. For example, when a user walks the accelerometer may measure a movement of more than 1 cm, when the accelerometer detects a user heart beat the accelerometer may measure a displacement of between 4 mm and 1 cm, and when the accelerometer measures a displacement of 4 mm or less (e.g., a micro-movement). The micro-movements may be charted in wave form such that the micro-movements are charted with a peak and a valley.

The displacement values may assist a non-transitory computer readable medium or processor in isolating movements caused by multiple sources (e.g., heart beat and respiration). The processor may receive data from at least one of the accelerometer or gyroscope related to movements of the user. The processor may dynamically filter the data. The processor may analyze the acceleration data without regard to a position of the device relative to the user or a position of the user. The processor may filter out unwanted signals and isolate only desired signals. For example, the processor may learn which signals are of interest and the processor may analyze only those signals of interest. The processor may be in communication with or include a non-transitory computer-readable medium.

At least one of the upper or lower modules 110 or 150 can be configured to continuously collect data from a user using an inward facing sensor array. However, certain techniques can be employed to reduce power consumption and conserve battery life of device 100. For instance, only one of the upper or lower modules 110 or 150 may continuously collect information. The module may be continuously active, but may wait to collect information when conditions are such that accurate readings are most likely.

For example, when one or more accelerometers or gyroscopic components of device 100 indicate that a user is still, at rest, or sleeping, one or more sensors of at least one of the upper module 110 or lower module 150 may collect information from the user while artifacts resulting from physical movement are absent. The accelerometer or gyroscope may not begin reading until the heart rate of the user measured by another sensor is below a predetermined limit. For example, if the ECG or PPG demonstrates that the user is moving then, the accelerometer or gyroscope may not be turned on. In another example, the accelerometer or gyroscope may turn off if macro-movements are detected or a number of macro-movements are detected above a threshold amount (e.g., 5 or more per min, 10 or more per min, 20 or more per min, 30 or more per min, or 60 or more per minute). The processor may be configured to remove or filter out macro-movements. Thus, the accelerometer or gyroscope may only measure micro-movements if the macro-movements are below the threshold amount (e.g., 20 or less per minute, 10 or less per minute, 5 or less per minute, or 2 or less per minute). Thus, the accelerometer or gyroscope when set, placed, or configured to read micro-movements may only be activated when macro-movements are not present or when macro-movements are infrequent. The accelerometer or gyroscope may measure micro-movements and macro-movements simultaneously and the macro-movements may be considered outliers and may be removed from reporting. Data provided by at least one of the accelerometer or gyroscope may include an x-component, a y-component, a z-component, or a combination of the x/y/z-components within a coordinate system.

The physiological information from an upper module 110, a lower module 150, or both may be graphically displayed or represented by a waveform on a display (not shown) of the device 100. The graphical display may be provided as an output. The output may include physiological information of a user. For example, the information collected may be categorized and then graphically represented as an output or two or more outputs. The one or more outputs may be one or more waveforms, two or more waveforms, or three or more waveforms. The waveforms may be individually created. The waveforms may overlay one another. The waveforms may be created by categorizing the micro-movements. The micro-movements may be categorized by strength of the micro-movements, frequency of the micro-movements, duration of the micro-movements, or a combination thereof. The waveforms may be a one or more waveforms such as a sine wave or a sinusoidal pattern. The output may have a graph having a heart rate, for example. In another example, the output may have one graph having respiration signals and the other graph having a heart rate.

Figure 2:
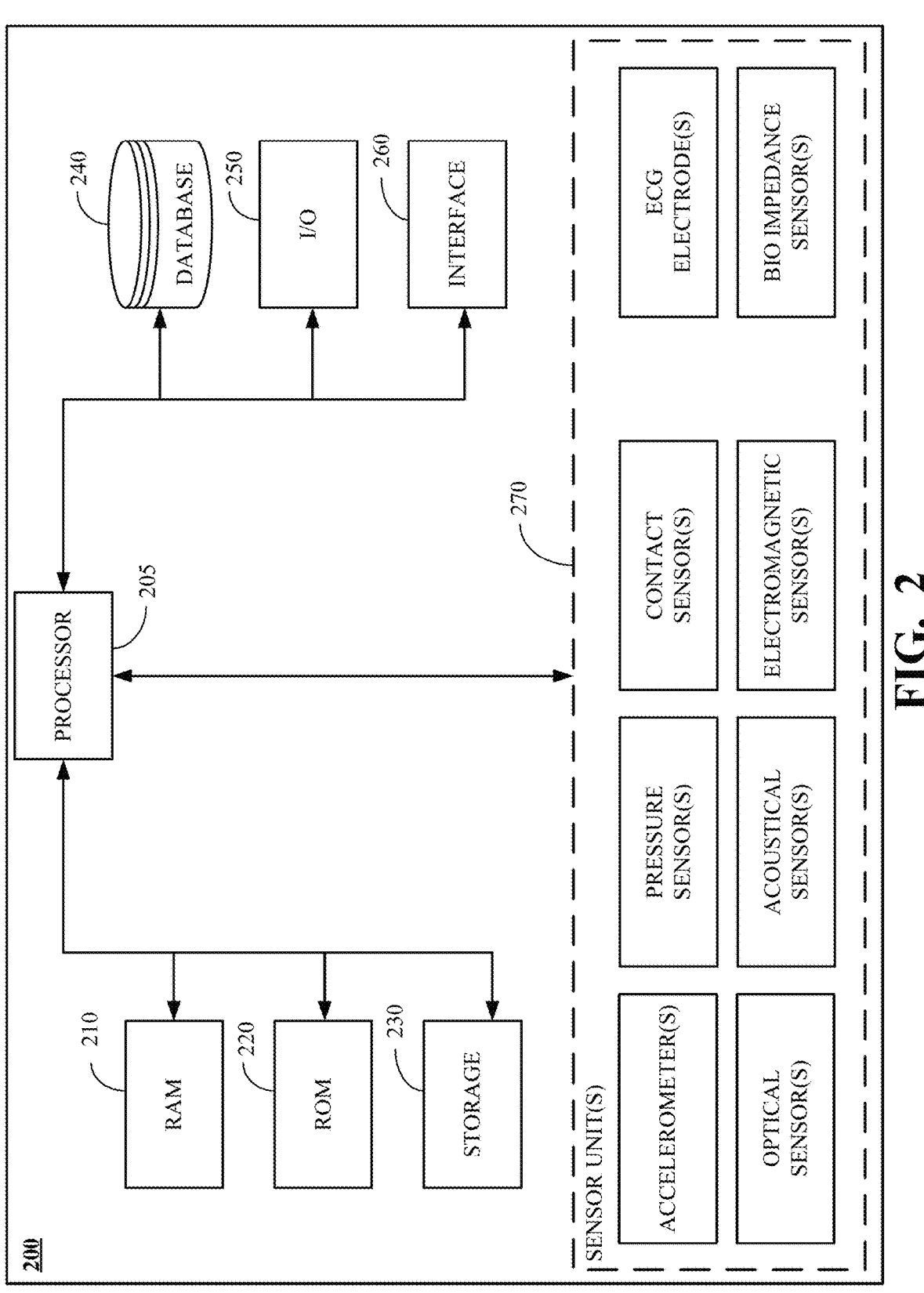
FIG. 2 depicts an example computing device according to some implementations of this disclosure.

FIG. 2 depicts an illustrative processor-based, computing device 200. The computing device 200 is representative of the type of computing device that may be present in or used in conjunction with at least some aspects of device 100, or any other device comprising electronic circuitry. For example, the computing device 200 may be used in conjunction with any one or more of transmitting signals to and from the one or more optical sensors or acoustical sensors, sensing or detecting signals received by one or more sensors of device 100, processing received signals from one or more components or modules of device 100 or a secondary device, and storing, transmitting, or displaying information. The computing device 200 is illustrative only and does not exclude the possibility of another processor- or controller-based system being used in or with any of the aforementioned aspects of device 100.

In one aspect, the computing device 200 may include one or more hardware and/or software components configured to execute software programs, such as software for obtaining, storing, processing, and analyzing signals, data, or both. For example, the computing device 200 may include one or more hardware components such as, for example, a processor 205, a random-access memory (RAM) 210, a read-only memory (ROM) 220, a storage 230, a database 240, one or more input/output (I/O) modules 250, an interface 260, and the one or more sensor modules 270. Alternatively and/or additionally, the computing device 200 may include one or more software components such as, for example, a computer-readable medium including computer-executable instructions for performing techniques or implement functions of tools consistent with certain disclosed embodiments. It is contemplated that one or more of the hardware components listed above may be implemented using software. For example, the storage 230 may include a software partition associated with one or more other hardware components of the computing device 200. The computing device 200 may include additional, fewer, and/or different components than those listed above. It is understood that the components listed above are illustrative only and not intended to be limiting or exclude suitable alternatives or additional components.

The processor 205 may include one or more processors, each configured to execute instructions and process data to perform one or more functions associated with the computing device 200. The term "processor," as generally used herein, refers to any logic processing unit, such as one or more central processing units (CPUs), digital signal processors (DSPs), application specific integrated circuits (ASICs), field programmable gate arrays (FPGAs), and similar devices. As illustrated in FIG. 2, the processor 205 may be communicatively coupled to the RAM 210, the ROM 220, the storage 230, the database 240, the I/O module 250, the interface 260, and the one or more sensor modules 270. The processor 205 may be configured to execute sequences of computer program instructions to perform various processes, which will be described in detail below. The computer program instructions may be loaded into the RAM 210 for execution by the processor 205.

The RAM 210 and the ROM 220 may each include one or more devices for storing information associated with an operation of the computing device 200 and/or the processor 205. For example, the ROM 220 may include a memory device configured to access and store information associated with the computing device 200, including information for identifying. initializing, and monitoring the operation of one or more components and subsystems of the computing device 200. The RAM 210 may include a memory device for storing data associated with one or more operations of the processor 205. For example, the ROM 220 may load instructions into the RAM 210 for execution by the processor 205.

The storage 230 may include any type of storage device configured to store information that the processor 205 may use to perform processes consistent with the disclosed embodiments.

The database 240 may include one or more software and/or hardware components that cooperate to store, organize, sort, filter, and/or arrange data used by the computing device 200 and/or the processor 205. For example, the database 240 may include user profile information, historical activity and user-specific information, physiological parameter information, predetermined menu/display options, and other user preferences. Alternatively, the database 240 may store additional and/or different information.

The I/O module 250 may include one or more components configured to communicate information with a user associated with the computing device 200. For example, the I/O module 250 may include one or more buttons, switches, or touchscreens to allow a user to input parameters associated with the computing device 200. The I/O module 250 may also include a display including a graphical user interface (GUI) and/or one or more light sources for outputting information to the user. The I/O module 250 may also include one or more communication channels for connecting the computing device 200 to one or more secondary or peripheral devices such as, for example, a desktop computer, a laptop, a tablet, a smart phone, a flash drive, or a printer, to allow a user to input data to or output data from the computing device 200.

The Interface 260 may include one or more components configured to transmit and receive data via a communication network, such as the Internet, a local area network, a workstation peer-to-peer network, a direct link network, a wireless network, or any other suitable communication channel. For example, the interface 260 may include one or more modulators, demodulators, multiplexers, demultiplexers, network communication devices, wireless devices, antennas, modems, and any other type of device configured to enable data communication via a communication network.

The computing device 200 may further include the one or more sensor modules 270. In one embodiment, the one or more sensor modules 270 may include one or more of an accelerometer module, an optical sensor module, an acoustical sensor module, and/or an ambient light sensor module. Of course, these sensors are only illustrative of a few possibilities and the one or more sensor modules 270 may include alternative or additional sensor modules suitable for use in the device 100. It should be noted that although one or more sensor modules are described collectively as the one or more sensor modules 270, any one or more sensors or sensor modules within device 100 may operate independently of any one or more other sensors or sensor modules. Moreover, in addition to collecting, transmitting, and receiving signals or information to and from the one or more sensor modules 270 at the processor 205, any the one or more sensors of the one or more sensor module 270 may be configured to collect, transmit, or receive signals or information to and from other components or modules of the computing device 200, including but not limited to the database 240, the I/O module 250, or the interface 260.

As described above with respect to FIG. 1, the one or more accelerometers of the device 100 can be used to detect large-scale motions of a subject indicative of physical activity (e.g., steps, running, walking, swimming, etc.). The same accelerometers can be used to determine the onset of a sleep period through the detection of a lack of motion. The one or more acoustical sensors can be used to detect and monitor heart rate. However, the sensitivity of the acoustical sensor(s) that detect heart rate aren't sensitive enough to detect relatively slow heart rate during sleeping. In one embodiment, upon determining that the subject is engaged in sleep, the sensitivity of the acoustical sensor(s) can be reconfigured to detect significantly low heart rate. Alternatively, the device 100 may include one or more acoustical sensors that are dedicated to, and configured for, detecting relatively slow heart rate during sleeping while one or more other acoustical sensors are used to detect regular heart rate during physical activity. To detect heart rate, an acoustical sensor can be configured to increase its sensitivity and sampling rate. Additionally, it may be advantageous to increase the sampling rate of an acoustical sensors for measuring relative slow heart rate during sleeping as compared to when measuring heart rate during physical activity. Again, regardless of the disparate sensitivity and/or sampling frequency between acoustical sensor settings for measuring regular and relative slow heart rate, the same acoustical sensor(s) in the device 100 of FIG. 1 can either be reconfigured upon detection of a sleep state, or alterative acoustical sensor(s) having a higher sensitivity can be activated during the sleep state. If an acoustical sensor that is calibrated for measuring regular heart rate during physical activity is used to measure relatively slow heart rate during sleeping, the amplitude of the output signal will not be great enough for accurate analysis. Conversely, if an acoustical sensor calibrated for measuring relatively slow heart rate during sleeping is used to measure regular heart rate during physical activity, the amplitude of the output signal will always be very large, resulting in a saturated signal that provides little useful information.

FIG. 3 is a flowchart of an example process 300 of acute stressors detection according to some implementations of this disclosure. The process 300 can be implemented as software and/or hardware modules in the computing device 200 in FIG. 2. For example, the process 300 can be implemented as software modules stored in the storage 230 as instructions and/or data executable by the processor 205 of an apparatus, such as the device 100 in FIG. 1. In another example, the process 300 can be implemented in hardware as a specialized chip storing instructions executable by the specialized chip. Some or all of the operations of the process 300 can be implemented by the processor 205 in FIG. 2. As described above, a person skilled in the art will note that all or a portion of the aspects of the disclosure described herein can be implemented using a general-purpose computer/processor with a computer program that, when executed, carries out any of the respective techniques, algorithms, and/or instructions described herein. In addition, or alternatively, for example, a special-purpose computer/processor, which can contain specialized hardware for carrying out any of the techniques, algorithms, or instructions described herein, can be utilized.

At an operation 302, heart rate variability (HRV) data determined based on an HRV-related metric associated with an individual can be obtained for acute stressors detection. As discussed above, the HRV data, which relates to physiological measure of fluctuations of time intervals between heartbeats, can be used to understand the balance of the nervous systems of the individual, and to provide indications about the overall physical health of the individual. A high HRV value or score indicates that the body is responsive to both the parasympathetic and sympathetic nervous systems. This means that the nervous system is balanced, and therefore the body can adapt to the environment as well as perform well. For example, a higher HRV score at rest is associated with better health. A low HRV score often means that one nervous system (such as the parasympathetic or the sympathetic nervous system) is dominating and sending stronger signals to the heart than the other nervous system (such as the other one of the parasympathetic or the sympathetic nervous system).

For example, it is often the case that the dominating nervous system is the sympathetic nervous system when the HRV score is low. If the HRV score is low during exercise (e.g., running, cycling), since the body is supposed to focus on allocating its resources to each part of the body such as the leg, which would be a sympathetic activity, the low HRV score might not impose a health risk. For example, intense workouts can cause reductions in the HRV score. However, if the low HRV score happens while the individual is resting, this would suggest that the body is working hard for some other things, such as, for example, stress, fatigue, dehydration, or sickness etc., leaving fewer resources available for exercising, competing, or being hard-working. Therefore, the process 300 can include informing the individual to take a break when the HRV score is low.

The HRV data can be determined from data collected by the device 100, such as a smart watch, for example. Data collected by the device 100 can be obtained, for example, by the processor 205. The data collected by the device 100 can be physiological information such as, for example, ECG, PPG, other heart rate-related information of the individual, or any other types of data collected the device 100. For example, the data collected by the device 100 can also include timestamp, accelerometer data, other sensor data, or a combination of the above. The data collected by the device 100 can be used to determine physiological parameters such as, for example, heart rates, HRV scores, parameters associated with sleep or exercise, or a combination of the above. In some implementations, the HRV data can be a measure of variation in time between each heartbeat. For example, the HRV data can include an HRV score and an HRV baseline. The HRV data can be determined, for example, according to heart rate data obtained from the user at a specific time period of a day, such as, for example, during sleep, or when the user wakes up from the sleep.

Figure 4:
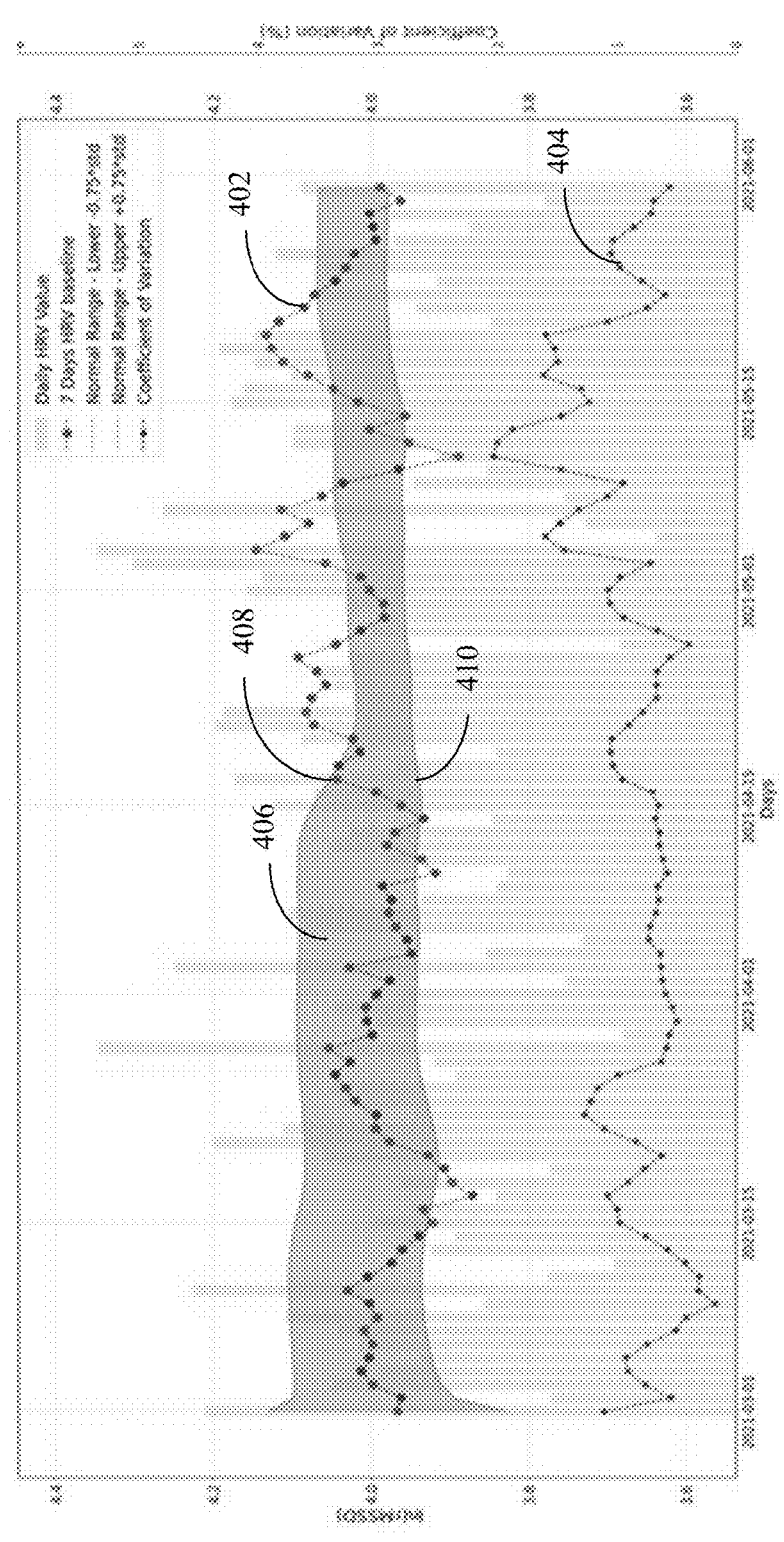
FIG. 4 is an example of heart rate variability (HRV) data over time according to some implementations of this disclosure.

In some implementations, the HRV data can have a high day-to-day variability. More specifically, the HRV data is affected by lifestyle factors that can be unique to an individual, so each individual can have a unique day-to-day HRV fluctuation. An example of heart rate variability (HRV) data over time is shown in FIG. 4. The daily HRV scores are shown as vertical bars. As can be seen, the daily HRV scores change from day to day, which can be based on the level of activity and amount of, for example, work-related stress.

To make effective use of the HRV data, the HRV data is interpreted with respect to the historical data of the individual, and changes that require further attention can be identified. Implementations of this disclosure go beyond providing confirmation of positive or negative adaption to the acute stressors to further identify a potentially bad lifestyle that might have negatively affected the physiological condition of the individual.

The HRV data can be determined based on an HRV-related metric, and the HRV-related metric can be determined from data collected by the device 100, such as the smart watch. In some implementations, the HRV-related metric comprises a root mean square of successive time differences (RMSSD) of consecutive heartbeats. A logarithm form of the RMSSD, such as In(RMSSD), can be used.

In some implementations, the HRV data can include, for example, an HRV baseline. The HRV baseline is indicative of a moving average of the HRV data during a first number of days. The HRV baseline is determined based on a time window T, the first number of days, and the HRV-related metric, such as, for example, In(RMSSD). The HRV baseline, which is based on the HRV-related metric, reflects a moving average of the HRV data across multiple days, for example, five days, seven days, and so forth. For example, in FIG. 4, line graph 402 indicates the 7-day based HRV baseline across different dates.

In some implementations, the HRV data can also include a smallest worthwhile change (SWC) indicative of a value range for the HRV-related metrics during a second number of days. The SWC can be determined based on a standard deviation of the HRV data during the second number of days, and the HRV-related metric, such as, for example, In(RMSSD). In some implementations, the SWC can provide the HRV value range during the consecutive multiple days, for example, 30 days, 60 days, and so forth. The SWC can have a lower bound and an upper bound for the HRV value range during the consecutive multiple days. Compared with the daily HRV score and the HRV baseline, the SWC can provide a flexible HRV value range that is useful for identifying the HRV's changes over a longer time range (e.g., 30 days, 60 days, or 90 days). For example, in FIG. 4, the SWC can be calculated to evaluate the individual's HRV changes using the daily HRV scores for a certain time range. The SWC is shown as a shaded area 406 with an upper bound 408 and a lower bound 410, and the c set as 0.75 in this example. The calculation of the SWC is further discussed below in connection with FIG. 4.

In some implementations, the HRV data can also include a coefficient of variation (CV) indicative of a value for assessing adaptation to a fitness program or a lifestyle change by the individual. The CV is determined based on the standard deviation of the HRV-related metric during a third number of days, the third number of days, and the HRV-related metric. In some implementations, the CV uses statistics to evaluate variation in averages, as will be discussed in connection with FIG. 4. For example, in terms of the HRV data, the CV can relate to variation in the HRV data between weeks, which is different from the HRV baseline which is focusing on the HRV data over a week. In some cases, if the CV of the individual is in a normal domain, the individual can easily adapt to a lifestyle change, e.g., a new fitness program. For example, in FIG. 4, a line graph 404 is used to illustrate the CV across different dates.

FIG. 4 illustrates an example of heart rate variability (HRV) data over time according to some implementations of this disclosure. In FIG. 4, the horizontal axis represents a time domain (e.g., from Mar. 1, 2021 to Jun. 1, 2021), and the vertical axis represents an HRV-related metrics to be used in the HRV analysis, such as In(RMSSD) in this example. RMSSD is considered a highly relevant and accurate measure of Autonomic Nervous System (ANS) activity over a short term. The RMSSD between consecutive heartbeats can be obtained by first calculating each successive time difference between heartbeats in millisecond. Then each of the values can be squared and the result can be averaged before the square root of the total is obtained. Empirically, In(RMSSD) is not significantly influenced by breathing frequency, unlike other metrics, and is therefore more suited to ambulatory measures and can be used to capture levels of parasympathetic activity over a short time frame.

For example, In(RMSSD) can be used to estimate the following HRV data: HRV baseline, smallest worth change (SWC), coefficient of variation (CV), and daily HRV score. Other HRV data can also be derived based on RMSSD or other HRV-related metrics, which can be used for further analysis. Some of the HRV data are also sometimes referred to herein as HRV trends as they tend to show the HRV trends over a multi-day time period. The HRV data, which can include some or all of the daily HRV score, the HRV baseline, the SWC, and the CV, can be updated based on the current day's HRV-related metric.

The HRV data can include the HRV baseline. The HRV baseline can be determined as a moving average of the HRV-related metrics during K consecutive days. For example, when the HRV-related metrics is In(RMSSD), the HRV baseline can be determined as $$\frac{X_t + X_{t-1} + \dots + X_{t-K}}{K},$$

wherein X is In(RMSSD), K is the number of consecutive days used for determining the HRV baseline, and t represents the current day.

The HRV data can include Smallest worth change (SWC). Smallest worth change (SWC) is indicative of a value range for the HRV-related metrics during N consecutive days (e.g., 30 days or 60 days). The SWC can be calculated as $$\frac{X_t \times X_{t-1} + \dots + X_{t-N+1}}{N} \pm c \times \sigma$$

wherein N is the number of consecutive days used for determining the SWC, and σ is a standard deviation of the HRV-related metrics during the N consecutive days. The SWC is a range with an upper bound of $$\frac{X_t + X_{t-1} + \dots + X_{t-N+1}}{N} + c \times \sigma$$

and a lower bound of $$\frac{X_t + X_{t-1} + \dots + X_{t-N+1}}{N} - c \times \sigma.$$

Constant c can be set as 0.5 or other values, such as, for example, 0.75 to make a broader range for SWC or 0.25 for a narrower range for SWC.

The HRV data can include Coefficient of variation (CV). Coefficient of variation (CV) is a value for assessing adaptation to a new fitness program or a lifestyle change by the individual. The CV can be determined as $$\frac{\sigma \times 100}{\dfrac{X_t + X_{t-1} + \dots + X_{t-M+1}}{M}},$$

wherein M is the number of consecutive days used for determining the CV, and $\sigma$ is a standard deviation of the HRV-related metrics during the M consecutive days. For example, M can be set as, for example, 7 or 14 days.

The HRV data can include daily HRV scores. The daily HRV scores used for determining the acute stressors can be determined as an average of ln(RMSSD) during sleep in a day for the individual, for example. For example, the daily HRV score can include the daily HRV score of today, or the daily HRV score of yesterday.

Back to FIG. 3, at an operation 304, it can be determined whether an HRV event indicative of a maladaptation risk of the individual has occurred based on the HRV data. The HRV event can be determined based on one or more rules and the HRV data. The HRV event indicative of the maladaptation risk can be used to indicate that the individual may suffer a lot of stress and fatigue. In that case, the individual will likely not be able to adapt to intense training and extra work assignment. When there is the maladaptation risk, it can be risky for the individual to continue to perform high-intensity work, training, or sports, since the individual's physiological condition is unable to promptly cope with the stress or fatigue.

In some implementations, the maladaptation risk is associated with at least one of the following states of the individual: inability to respond to the acute stressors, poor adaptation to work, or non-functional overreaching.

In some implementations, the SWC, the daily HRV score, and the HRV baseline associated with the HRV data can be used to determine whether the HRV event indicative of the maladaptation risk of the individual has occurred. For example, the HRV event indicative of the maladaptation risk of the individual can be determined to have occurred when the daily HRV score of the current day and the HRV baseline are outside of the ranges in the SWC. Other rules and examples are described below in connection with FIG. 4.

In some implementations, historical HRV data is obtained, and the current HRV data is compared to the historical HRV data and the change trend of the HRV data is determined. The historical HRV data can be obtained from local storage space or from another device. The historical HRV data can include, for example, HRV data of at least one day before today or yesterday, such as 7 days, 21 days, or one month. In some examples, the HRV data can be stored locally, or can be sent to a server device or another device for storage.

FIG. 4 shows the example HRV data for a sample user over three months (from Mar. 1, 2021 to Jun. 1, 2021). Line graph 402 indicates the 7-day based HRV baseline across different dates. Line graph 404 indicates the CV across different dates. The SWC is shown as a shaded area 406 with an upper bound 408 and a lower bound 410, with the c set as 0.75 in this example. For example, when the HRV baseline is less than the lower bound of the SWC, there can be significantly high stress for the individual. In that case, the individual can be advised to reduce the training intensity from, for example, "high" or "moderate" level to "easy" or "rest" level to recovery from fatigue.

In some implementations, based on the HRV data, one or more rules as follows can be used to determine whether an HRV event indicative of the maladaptation risk of the individual has occurred for an individual:

When the HRV baseline is greater than the upper bound of the SWC, the individual's body shows positive adaptation to stressors. There is no HRV event indicative of the maladaptation risk.

When the HRV baseline is within the range of the SWC, the individual's physiological condition is normal from a cardiac autonomic nervous system perspective. There is no HRV event indicative of the maladaptation risk. It can be said that there is no relevant trend for the HRV event.

When the HRV baseline is lower than the lower bound of the SWC, it can be determined that the individual might be experiencing significant stress. It can be recommended to the individual that the training intensity should go from high or moderate to easy or rest (for faster recovery).

When HRV baseline<Daily HRV score<Lower bound of SWC, there might be a significant stressor such as an acute stressor. It can be recommended to the individual that the training intensity should go from high or moderate to easy or rest (for faster recovery).

When Lower bound of SWC<Daily HRV score<HRV Baseline, the individual's physiological condition is normal on a day-to-day basis from a cardiac autonomic nervous system perspective. There is no HRV event indicative of the maladaptation risk. It can be said that there is no relevant trend for the HRV event.

When the CV increases, and the HRV baseline increases, it can be determined that the individual is going though greater stress, fatigue, lower fitness, or poor adaption. This can be used to show the maladaptation to training. It can be determined that the HRV event indicative of the maladaptation risk has occurred for the individual. Therefore, recovery strategies can be recommended to the individual, such as, for example, strategies based on sleep, diet, yoga, or other ways to reduce non-training related stress.

When the daily HRV score and the HRV baseline are outside of the ranges in the SWC. the HRV baseline is not greater than the upper bound HRV value in the SWC, and the HRV baseline decreases, it can be determined that the HRV event indicative of the maladaptation risk has occurred for the individual.

When the HRV baseline is lower than the lower bound of the SWC, or that the HRV baseline decreases, this shows the individual is unable to respond to stressors and there is a risk of non-functional overreaching. It can be determined that the HRV event indicative of the maladaptation risk has occurred for the individual.

Increased HRV Baseline shows that the individual is most likely coping well with the increased load.

Decreased HRV Baseline shows that the individual shows significantly higher stress and recovery should be prioritized.

When both the CV and the HRV baseline increase, it shows that the individual's physiological condition can cope well with stressors and there is no HRV event indicative of the maladaptation risk.

When the CV decreases and the HRV baseline increases, the individual's physiological condition is positive adaptation to stressors. There is no HRV event indicative of the maladaptation risk.

In some implementations, the following rules can be implemented in an example algorithm for HRV event classification.

IF the daily HRV score is in the Normal Range (e.g., the range of SWC) and the HRV baseline is in the Normal Range:

Return "No Relevant Trends" ELSE IF the HRV baseline is greater than the upper bound of the Normal Range:

Return "Positive Adaptation to Stressors" ELSE IF the CV is increased and the HRV baseline is increased:

Return "Most Likely Coping well with Stressors" ELSE IF the CV is decreased and the HRV baseline is increased:

Return "Positive Adaptation to Stressor" ELSE IF the CV is decreased and the HRV baseline is decreased:

Return "Risk of Maladaptation" ELSE IF the CV is increased and the HRV baseline is decreased:

Return "Risk of Maladaptation" ELSE

Return "Other"

For example, based on the various HRV data, the HRV events can be classified as "No Relevant Trends," "Positive Adaptation to Stressors," "Most Likely Coping well with Stressors," "Positive Adaptation to Stressor," "Risk of Maladaptation" (which shows that the HRV event indicative of the maladaptation risk has occurred), "Other" etc.

In one example, for the individual, the HRV event indicative of the maladaptation risk has occurred when the following three conditions are satisfied: (a) the current day's HRV value and the HRV baseline are outside of the ranges in the SWC, (b) the HRV baseline is not greater than the upper bound HRV value in the SWC, and (c) the HRV baseline decreases with current day's HRV value.

Back to FIG. 3, at an operation 306, responsive to determining that the HRV event indicative of the maladaptation risk of the individual has occurred, a causal inference engine is used to determine at least one acute stressor as a probable cause of the HRV event based on inputs comprising the HRV event and lifestyle data associated with the individual. The lifestyle data comprises at least one lifestyle event and environmental contexts associated with the at least one lifestyle event performed by the individual. In some implementations, the lifestyle data can be collected by devices, for example, by a device 100 (e.g., a smart watch or physiological monitor). The lifestyle data can include lifestyle events and corresponding environmental contexts. Environmental contexts associated with at least one lifestyle event performed by the individual can also include, for example, contexts extracted from workout data of the device 100, such as, for example, exercise types, duration, timestamp, air pollution, air temperature, pollen count etc. When the HRV event has occurred, the lifestyle events can be the reason why the HRV event has occurred.

At the operation 306, the acute stressor can be determined as a lifestyle event that causes the HRV event indicative of the maladaptation risk that the individual needs to avoid. The HRV event, along with the lifestyle events and the environmental contexts, can be inputs to detect the at least one acute stressor. In some implementations, acute stressors can include events that negatively affect the individual's physiology in the immediate future (e.g., an event that has an effect on the individual's physiology which lasts from a few minutes up to 24-48 hours). For example, acute stressors can include, for example, intense workout, an intercontinental flight, a night out with too many drinks, high caffeine intake, etc.

Figure 6:
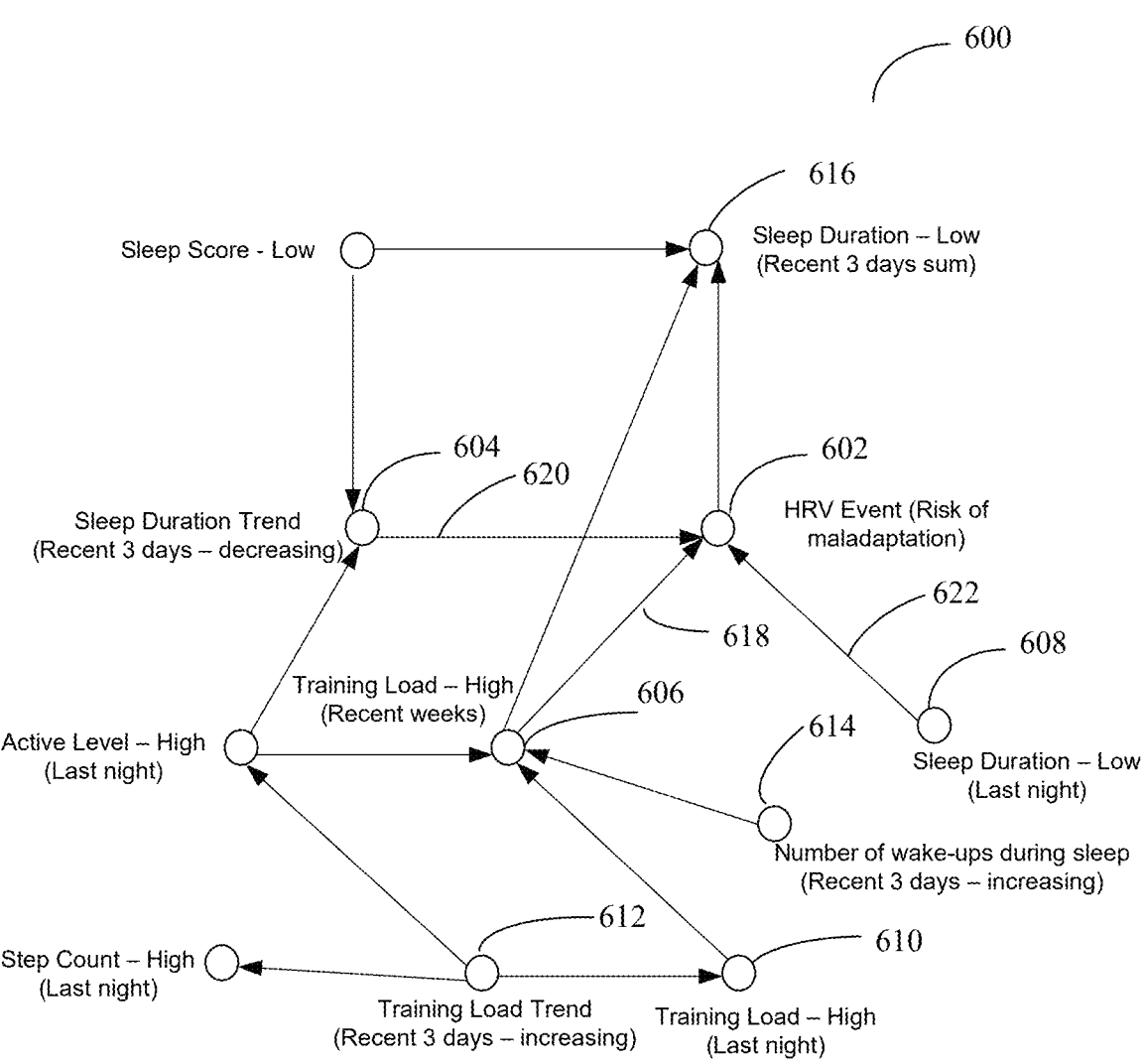
FIG. 6 is an example of a directed acyclic graph (DAG) for acute stressors detection according to some implementations of this disclosure.

In some implementations, the at least one acute stressor is associated with at least one of the following lifestyle events of the individual: lower than normal sleep duration, higher than normal workout, decreasing sleep duration, or higher than normal training load. In some implementations, the at least one acute stressor comprise at least one of: lower than normal sleep duration, higher than normal workout, decreasing sleep duration during consecutive days, or higher than normal training load. In the example of FIG. 6, an acute stressor can be determined from the causally related lifestyle events (represented by, for example, nodes 604, 608 and 610) as the probable cause of the HRV event.

In some implementations, the lifestyle events comprise at least one of exercise events or sleep events for the individual. such as, for example, workout at night, low sleep duration yesterday, high load training in the morning, and so forth. For example, FIG. 6 illustrates several lifestyle events, such as a sleep event 604 indicating a sleep duration trend decreasing (e.g., sleep duration decreases in recent 3 days), an exercise event 606 indicating high training load (e.g., training load is high in recent 6 weeks), and a sleep event 608 indicating that sleep duration for the individual last night is low. These lifestyle events can cause an HRV event 602 indicative of the maladaptation risk.

To model the exercise events, TRIMP (Training Impulse) can be used. TRIMP is a weighted product of training volume and training intensity. In one example, based on a daily TRIMP score, Fitness Level of the individual can be defined as an average TRIMP score for the last several (e.g., 6) weeks and Fatigue Level of the individual can be defined as an average TRIMP score for the last week. With Fitness Level and Fatigue Level, Training Stress Balance of the individual can be determined as the difference between Fitness Level and Fatigue Level, which characterizes the training status of the individual.

To model the sleep events, sleep analysis can be performed to recognize stages such as deep sleep, light sleep, REM sleep, wake-up, etc. Additionally, environmental contexts such as the number of times an individual wakes up during core sleep, sleep start time, deep sleep ratio, effective sleep duration, sleeping latency, length of bedtime, and the number of REM cycles can be used. A sleep score can be provided to quantify sleep quality of the individual.

The causal relationship between the HRV data and the individual's lifestyle events can be determined by finding statistical dependencies. The at least one acute stressor can be determined as a probable cause of the HRV event using a causal inference engine. To determine the direction of causality and which lifestyle events caused the HRV event indicative of the maladaptation risk of the individual, probability theory (such as Bayes theorem) can be used.

For example, Bayesian Network (BN) (e.g., Bayesian graphical models) can be used to visualize the statistical dependencies between variables. For example, two random variables X and Y are statistically dependent (XIY), then one of the following is true: (a) X causes Y, (b) Y causes X, or (c) there exists a third variable Z that causes both X and Y. Further, (d) X and Y become independent given Z, i.e., $X \perp Y|Z$. Based on this definition, causation can represent that one (independent) variable causes the other (dependent) variable.

In some implementations, using the causal inference engine includes using a directed acyclic graph (DAG) to determine statistical dependencies between a first node representing a causally related lifestyle event and a second node representing the HRV event, in which an edge is established from the first node to the second node upon determining that the causally related lifestyle event associated with the first node is likely to have caused the HRV event associated with the second node. Here a weight of the edge can be used to indicate a conditional probability P. For example, an edge can be represented by P(the HRV event | the causally related lifestyle event), which indicates the probability of the HRV event occurring based on occurrence of the causally related lifestyle event occurs. Each node in the DAG represents a lifestyle event (such as exercise events or sleep events) or an HRV event (such as an HRV event indicative of the maladaptation risk). An example of the DAG for acute stressors detection is shown in FIG. 6.

In some implementations, the recent Y days' data (also referred to as "observations") are collected for the individual. After that, the DAG that best captures the causal dependencies between the environmental contexts and lifestyle events is searched. To improve the efficiency, since the time complexity of constructing the DAG from enumeration can be significantly high, a score-based structure learning technique (e.g., Bayesian Dirichlet, or Bayesian Information Criterion) with a search algorithm (e.g., Hill Climb Search, Chow-Liu, or Tree-augmented Naive Bayes) can be applied to construct the DAG to be searched. Once this DAG is constructed, it is possible to use to the DAG to get an answer to a question, such as "what-if-we-did-X", through causal inference. To make inferences, Conditional Probabilistic Tables (CPTs) can be used, for example. These tables can be computed by parameter learning in the DAG by using a technique such as Maximum Likelihood Estimation or Bayesian Estimation. An example CPT and using the DAG for acute stressors detection is described below in connection with FIG. 6.

In some implementations, maximum likelihood estimation can be used to determine the at least one acute stressor as the probable cause of the HRV event, for example, from the plurality of casually related lifestyle events. For example, the parameters can be estimated based on an assumed probability distribution, given some observed data. By maximizing a likelihood function so that, under the statistical model, the at least one acute stressor associated with the observed data that is most probable is selected as the at least one acute stress as the probable cause.

In some implementations, Bayesian estimation can be used to determine the at least one acute stressor as the probable cause of the HRV event. For example, an estimator or decision rule that minimizes the posterior expected value of a loss function can be used.

In some implementations, the at least one acute stressor as the probable cause of the HRV event is selected from a plurality of causally related lifestyle events, wherein each of the plurality of causally related lifestyle events is associated with a respective edge to the HRV event on the DAG.

Figure 5:
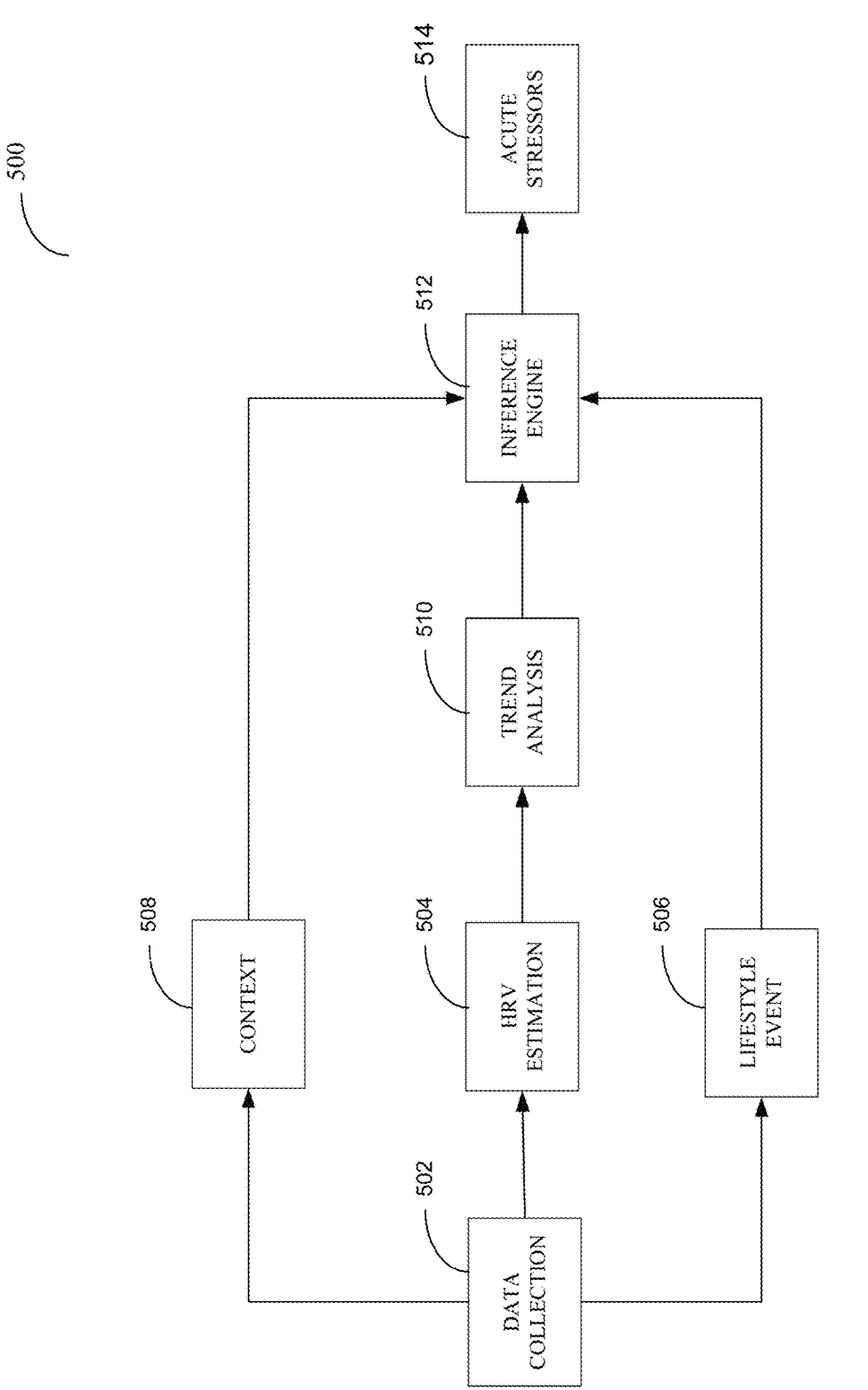
FIG. 5 is an example of using causal inference for acute stressors detection according to some implementations of this disclosure.

FIG. 5 is an example of using causal inference for acute stressors detection according to some implementations of this disclosure.

At an operation 502, data, such as sensor data, can be collected for an individual. The data can be collected by a processor such as the processor 205 of a device, e.g., the device 100 in FIG. 1, for acute stressors detection. The data collected by the device 100 can include physiological information such as, for example, ECG, PPG, other heart rate-related information of the individual, or any other types of data collected the device 100. For example, the data collected by the device 100 can also include timestamp, accelerometer data, other sensor data, or a combination of the above. The data collected by the device 100 can be used to determine physiological parameters such as, for example, heart rates, HRV scores, parameters associated with sleep or exercise, or a combination of the above. In some implementations, HRV data and lifestyle data associated with the individual are derived from the data collected by the device 100. The HRV data and the lifestyle data, as previously discussed, can be used to indicate the individual's physiological condition. At an operation 504, the data collected at the operation 502 for the individual can be used to estimate an HRV-related metric. In some implementations, the HRV-related metric comprises a root mean square of successive time differences (RMSSD) of consecutive heartbeats. A logarithm form of the RMSSD, such as ln(RMSSD), can be used. The HRV-related metric can be used for determining the daily HRV score. For example, the daily HRV score can be determined as an average of ln(RMSSD) during sleep in a day for the individual. Further, the HRV-related metric can be used to determine HRV trend data at an operation 510.

At an operation 506, data regarding the lifestyle events can be extracted from the data collected at the operation 502. In some implementations, the lifestyle events can include at least one of exercise events or sleep events. For example, lifestyle events can be associated with "workout", "low sleep duration" "high load training" among others.

For example, logs of relevant data streams can be collected at the operation 502 for understanding and building personal model and for detecting acute stressors. In the context of wearable sensing technology, events can be obtained using a device. Each data stream from device can be analyzed to detect events from the data stream. In addition, events can be observed and recorded by the individual or an observer. Data associated with the events (also referred to as "event data") can include, for example, information regarding what, when, and how an event occurs. Data associated with the events can be centered around the individual, indexed, and chronicled with relevant data about the individual. Generating event data often requires domain knowledge from specific fields such as medicine, physiology, and sleep science, etc. For example, heart rate with a numerical value at a particular time in an exercise training application can be classified as low, medium, and high using a specific algorithm that takes into consideration the individual and the context at the particular time. For example, an example event data for a heart rate event can include, for example, "high heart rate 30 minutes last night," which is a combination of what, when, and how the event occurs, as discussed above.

At an operation 508, contexts associated with at least one lifestyle event can be extracted from the data collected at the operation 502. In some implementations, the contexts can include information about the space and time in which the individual performs the lifestyle events. For example, the individual can perform workouts at night or in the morning. In some implementations, the contexts can include, for example, environmental contexts associated with at least one lifestyle event performed by the individual, which can include, for example, contexts extracted from workout data of the device 100, such as, for example, exercise types, duration, timestamp etc. The contexts can also include, for example, accelerometer data, or other sensor data.

At an operation 510, trend analysis can be performed on the data collected at the operation 502 and the HRV-related metric estimated at the operation 504. As described above in connection with FIGS. 3 and 4, the HRV data can be determined based on an HRV-related metric. The HRV data can include, for example, at least one of the daily HRV score, the HRV baseline, the smallest worth change (SWC), or the coefficient of variation (CV). Each of the HRV baseline, the SWC, and the CV is associated with a specific number of days, which reflects the HRV trends over time. Other types of the HRV data can also be determined and used as inputs for the next operation.

At an operation 512, the lifestyle events extracted at the operation 506, such as the exercise events and the sleep events, and the contexts extracted at the operation 508, along with the HRV event determined at the operation 510 can be inputs to an inference engine to detect the acute stressors. For example, the lifestyle events and the contexts can include, for example, "workout at night", "low sleep duration yesterday", "high load training in the morning." and so forth.

In some implementations, one or more rules discussed above in connection with FIGS. 3 and 4 can be used to determine whether an HRV event indicative of a maladaptation risk of the individual has occurred based on the HRV data, (e.g., the daily HRV score, the HRV baseline, the SWC or the CV). As an example, when the daily HRV score and the HRV baseline are not in the SWC, the HRV baseline is not greater than the upper bound of the SWC, and the HRV baseline is decreased, it can be determined that the HRV event has occurred for the individual.

At the operation 512, responsive to determining that the HRV event indicative of the maladaptation risk of the individual has occurred, the inference engine can be used to determine at least one acute stressor as a probable cause of the HRV event based on inputs comprising the HRV event from the operation 510, the lifestyle events from the operation 508, and the environmental contexts from the operation 504. In some implementations, a directed acyclic graph (DAG) can be used to determine statistical dependencies between the lifestyle events from the operation 508 and the HRV event from the operation 510. In the DAG, an edge can be established between a first node and a second node upon determining that the causally related lifestyle event associated with the first node is likely to have caused the HRV event associated with the second node. Using FIG. 6 as an example, an HRV event 602 indicative of the maladaptation risk has occurred for the individual. An edge 618 is established between a lifestyle event 606 and the HRV event 602 in the DAG, which indicates the lifestyle event 606 can be an acute stressor that causes the HRV event 602. To determine which of the possible nodes is the acute stressor, in some implementations, a conditional probability table (CPT) or another statistical technique can be used. The CPT can be determined for the DAG, such as, the DAG 600, for example. In some implementations, the acute stressor can be determined by selecting a node from the nodes representing causally related lifestyle events as the probable cause of the HRV event. More details are described below in connection with FIG. 6.

At an operation 514, the at least one acute stressor can be notified to the individual. In some implementations, the at least one acute stressor can be summarized by at least one sentence that is notified to the individual. In some implementations, the at least one acute stressor can include multiple acute stressors that can be integrated into one result. For example, the output can be a combination of contents associated with the nodes 608 and 610, such as, for example, "the total sleep duration was low last night and hard workout was observed yesterday." In some examples, information about how to better cope with the at least one acute stressor is provided to the individual, which can include instructions such as, for example, "try to go to sleep before 10 PM," or "better to decrease the training load," etc.

FIG. 6 illustrates an example of a directed acyclic graph (DAG) 600 for acute stressors detection for a sample user according to some implementations of this disclosure. As previously described, a DAG includes nodes and edges with each edge directed from one node to another. In this example, the DAG 600 is constructed using the sample user's data (e.g., HRV events and lifestyle data) over a period of time.

According to the DAG 600 in FIG. 6, an HRV event indicative of a maladaptation risk of the individual (e.g., the sample user) is represented by a node 602. The other nodes represent lifestyle events, which include some exercise events and some sleep events. For example, a node 604 represents a sleep event indicating a sleep duration trend decreasing (e.g., sleep duration decreases in recent 3 days). A node 606 represents an exercise event indicating high training load (e.g., training load is high in recent 6 weeks). A node 608 represents a sleep event indicating that sleep duration for the individual last night is low. A node 610 represents an exercise event, which indicates that the training load for the individual is high last night.

In some implementations, in the DAG, such as the DAG 600, the lifestyle event is represented by a first node (e.g., the node 604) and the HRV event is represented by a second node (e.g., the node 602). When the conditional probability P (the HRV event | the lifestyle event) is greater than or equal to a probability threshold T, the lifestyle event can be referred to as a causally related lifestyle event, and an edge (e.g., an edge 620) is established between the first node representing the causally related lifestyle event (e.g., the node 604) and the second node representing the HRV event (e.g., the node 602). In that case, the causally related lifestyle event (e.g., sleep duration decreases in recent 3 days) associated with the first node (e.g., the node 604) is likely to have caused the HRV event indicative of the maladaptation risk of the individual, which is associated with the second node (e.g., the node 602).

In some implementations, as previously mentioned, estimation based on a probability theory (e.g., Bayes estimation or maximum likelihood estimation) can be used to determine which of the lifestyle event(s) had caused the HRV event. CPT can be determined by parameter learning in the DAG using these techniques (e.g., Bayes estimation or maximum likelihood estimation).

In some implementations, a score-based structure learning technique (e.g., Bayesian Dirichlet or Bayesian Information Criterion) with a search algorithm (e.g., Hill Climb Search, or Tree-augmented Naive Bayes) can be used to determine which of the lifestyle event(s) had caused the HRV event.

In some implementations, a score can be associated with each edge, and joint probability of a combination of events according to one possible DAG can be computed. The joint events for the edges of the DAG can be ranked by their scores, and events with higher probability can be obtained to determine the final DAG. Acute stressors can thus be determined according to the final DAG. The weight or probability of each edge can be determined according to, for example, historical lifestyle data. The joint probability of a DAG can be determined as the multiplication of all weights in the DAG.

To determine the causal dependencies between the lifestyle events and the HRV event, data for the lifestyle events and the HRV event from multiple days (e.g., HRV data and lifestyle data including the lifestyle events and corresponding environmental contexts) can be collected. Based on the collected data, as previously described, a conditional probability P (the HRV event | the lifestyle event) can be calculated for each lifestyle event.

In an illustrative example, the probability threshold T is assumed to be equal to 0.8. P (the HRV event associated with the node 602 | the lifestyle event associated with the node 604) is equal to 0.9. P (the HRV event associated with the 602 | the lifestyle event associated with the node 606) is equal to 0.8. P (the HRV event associated with the node 602 | the lifestyle event associated with the 608) is equal to 0.85. The conditional probabilities for these three lifestyle events are all greater than the probability threshold T (0.8 in this example). Therefore, in this example, the lifestyle events associated with the nodes 604, 606, and 608 can be referred to as the causally related lifestyle events.

In other words, using the DAG 600 to finding the statistics dependencies between the nodes can lead to the following three possible causes (e.g., the node 604, the node 606, and the node 610) as causally related lifestyle events for the HRV event represented by the node 602. Each of the nodes 604, 606, 608 has a directional edge to the node 602. The node 610 has a directional edge to the node 606.

Possible cause 1: The total sleep duration yesterday was low.

Possible cause 2: The total sleep duration has been decreasing for the last 3 days.

Possible cause 3: The hard workout was observed yesterday.

In this example, an acute stressor is determined from the nodes representing the causally related lifestyle events (e.g., the nodes 604, 608 and 610) as the probable cause of the HRV event associated with the node 602. Each of the causally related lifestyle events is associated with a respective edge to the HRV event on the DAG. For example, the node 604 is associated with the edge 620. The node 608 is associated with the edge 622.

To determine which of the possible nodes is the acute stressor, in some implementations, a conditional probability table (CPT) or another statistical technique can be used. The CPT can be determined for the DAG, such as, the DAG 600, for example. In this illustrating example, the following CPT can be used:

TABLE 1

| | Short Sleep Duration Yesterday | Decreasing Sleep Duration for the last 3 days | Hard Workout | Result (conditional Probability) |
|---|---|---|---|---|
| 1 | 0 | 0 | 0 | 0 |
| 2 | 0 | 1 | 0 | 0 |
| 3 | 0 | 0 | 1 | 1 |
| 4 | 0 | 1 | 1 | 1 |
| 5 | 1 | 0 | 0 | 0 |
| 6 | 1 | 0 | 1 | 0 |
| 7 | 1 | 1 | 0 | 0 |
| 8 | 1 | 1 | 1 | 0 |

In some implementations, an additional column can be added to the CPT to indicate frequency of occurrence. In this example, "Short Sleep Duration Yesterday" is "1" when the associated lifestyle event occurs, and so on. The events can be ranked with their frequencies. Other techniques using conditional probability can also be used.

In some implementations, the acute stressor can be determined by selecting a node (e.g., node 610 or 608) from the nodes representing causally related lifestyle events as the probable cause of the HRV event associated with the node 602. In this example, the node 610 indicates that the training load for the individual is high last night can be selected as the probable cause of the HRV event associated with the node 602.

In some implementations, the acute stressor selected as the probable cause of the HRV event associated with the node 602 can be provided to the individual in an interactive manner to reduce future acute stressors for the individual. For example, contents regarding the node 610 indicating "hard workout was observed yesterday" can be provided to the individual.

In some implementations, information regarding the acute stressor can be provided to the individual by integrating results from multiple possible nodes representing causally related lifestyle events. For example, the output can be a combination of contents associated with the nodes 608 and 610, such as, for example, "the total sleep duration was low and hard workout was observed yesterday."

The aspects of the disclosure described herein can be described in terms of functional block components and various processing operations. The disclosed processes and sequences may be performed alone or in any combination. Functional blocks can be realized by any number of hardware and/or software components that perform the specified functions. For example, the described aspects can employ various integrated circuit components, such as, for example, memory elements, processing elements, logic elements, look-up tables, and the like, which can carry out a variety of functions under the control of one or more microprocessors or other control devices. Similarly, where the elements of the described aspects are implemented using software programming or software elements, the disclosure can be implemented with any programming or scripting languages, such as C, C++, Java, assembler, or the like, with the various algorithms being implemented with any combination of data structures, objects, processes, routines, or other programming elements. Functional aspects can be implemented in algorithms that execute on one or more processors. Furthermore, the aspects of the disclosure could employ any number of conventional techniques for electronics configuration, signal processing and/or control, data processing, and the like. The words "mechanism" and "clement" are used broadly and are not limited to mechanical or physical implementations or aspects, but can include software routines in conjunction with processors, etc.

Implementations or portions of implementations of the above disclosure can take the form of a computer program product accessible from, for example, a computer-usable or computer-readable medium. A computer-usable or computer-readable medium can be any device that can, for example, tangibly contain, store, communicate, or transport a program or data structure for use by or in connection with any processor. The medium can be, for example, an electronic, magnetic, optical, electromagnetic, or semiconductor device. Other suitable mediums are also available. Such computer-usable or computer-readable media can be referred to as non-transitory memory or media and can include RAM or other volatile memory or storage devices that can change over time. A memory of an apparatus described herein, unless otherwise specified, does not have to be physically contained in the apparatus, but is one that can be accessed remotely by the apparatus, and does not have to be contiguous with other memory that might be physically contained in the apparatus.

Any of the individual or combined functions described herein as being performed as examples of the disclosure can be implemented using machine-readable instructions in the form of code for operation of any or any combination of the aforementioned hardware. The computational codes can be implemented in the form of one or more modules by which individual or combined functions can be performed as a computational tool, the input and output data of each module being passed to/from one or more further modules during operation of the methods and systems described herein.

Information, data, and signals can be represented using a variety of different technologies and techniques. For example, any data, instructions, commands, information, signals, bits, symbols, and chips referenced herein can be represented by voltages, currents, electromagnetic waves, magnetic fields or particles, optical fields or particles, other items, or a combination of the foregoing.

The word "example" is used herein to mean serving as an example, instance, or illustration. Any aspect or design described herein as "example" is not necessarily to be construed as being preferred or advantageous over other aspects or designs. Rather, use of the word "example" is intended to present concepts in a concrete fashion. Moreover, use of the term "an aspect" or "one aspect" throughout this disclosure is not intended to mean the same aspect or implementation unless described as such.

As used in this disclosure, the term "or" is intended to mean an inclusive "or" rather than an exclusive "or" for the two or more elements it conjoins. That is unless specified otherwise or clearly indicated otherwise by the context, "X includes A or B" is intended to mean any of the natural inclusive permutations thereof. In other words, if X includes A; X includes B; or X includes both A and B, then "X includes A or B" is satisfied under any of the foregoing instances. Similarly, "X includes one of A and B" is intended to be used as an equivalent of "X includes A or B." The term "and/or" as used in this disclosure is intended to mean an "and" or an inclusive "or." That is, unless specified otherwise or clearly indicated otherwise by the context, "X includes A, B, and/or C" is intended to mean that X can include any combinations of A, B, and C. In other words, if X includes A; X includes B; X includes C; X includes both A and B; X includes both B and C; X includes both A and C; or X includes all of A, B, and C, then "X includes A, B, and/or C" is satisfied under any of the foregoing instances. Similarly, "X includes at least one of A, B, and C" is intended to be used as an equivalent of "X includes A, B, and/or C."

The use of the terms "including" or "having" and variations thereof herein is meant to encompass the items listed thereafter and equivalents thereof as well as additional items. Depending on the context, the word "if" as used herein can be interpreted as "when," "while," or "in response to."

The use of the terms "a" and "an" and "the" and similar referents in the context of describing the disclosure (especially in the context of the following claims) should be construed to cover both the singular and the plural. Furthermore, unless otherwise indicated herein, the recitation of ranges of values herein is intended merely to serve as a shorthand method of referring individually to each separate value falling within the range, and each separate value is incorporated into the specification as if it were individually recited herein. Finally, the operations of all methods described herein are performable in any suitable order unless otherwise indicated herein or otherwise clearly contradicted by the context. The use of any and all examples, or language indicating that an example is being described (e.g., "such as"), provided herein is intended merely to better illuminate the disclosure and does not pose a limitation on the scope of the disclosure unless otherwise claimed.

This specification has been set forth with various headings and subheadings. These are included to enhance readability and ease the process of finding and referencing material in the specification. These headings and subheadings are not intended, and should not be used, to affect the interpretation of the claims or limit their scope in any way. The particular implementations shown and described herein are illustrative examples of the disclosure and are not intended to otherwise limit the scope of the disclosure in any way.

All references, including publications, patent applications, and patents, cited herein are hereby incorporated by reference to the same extent as if each reference were individually and specifically indicated as incorporated by reference and were set forth in its entirety herein.

While the disclosure has been described in connection with certain embodiments and implementations, it is to be understood that the disclosure is not to be limited to the disclosed implementations but, on the contrary, is intended to cover various modifications and equivalent arrangements included within the scope of the appended claims, which scope is to be accorded the broadest interpretation as is permitted under the law so as to encompass all such modifications and equivalent arrangements.

What is claimed is:

1. A method of acute stressors detection using a wearable device, comprising:

obtaining, by a processor associated with the wearable device, heart rate data collected by an inward facing heart rate sensor of the wearable device facing toward or in contact with an individual's skin when the wearable device is worn by the individual;

determining, by the processor, heart rate variability (HRV) data based on an HRV-related metric associated with the individual, wherein the HRV-related metric is derived from the heart rate data;

determining, based on the HRV data, whether an HRV event indicative of a maladaptation risk of the individual has occurred, wherein the HRV event indicative of the maladaptation risk is determined according to at least two different parameters from the HRV data, a first one of the at least two different parameters is derived from the HRV-related metric over time; and responsive to determining that the HRV event indicative of the maladaptation risk of the individual has occurred, determining, by the processor, at least one acute stressor as a probable cause of the HRV event using causal inference techniques based on the HRV event, at least one lifestyle event performed by the individual, and environmental contexts associated with the at least one lifestyle event, wherein the at least one acute stressor is determined by comparing statistical dependencies between the HRV event and each of the at least one lifestyle event, wherein the at least one lifestyle event and the environmental contexts are extracted from sensor data collected by the wearable device, and the sensor data comprises the heart rate data and at least one other type of sensor data collected by the wearable device, wherein the HRV data further comprises an HRV baseline and a smallest worthwhile change (SWC), the HRV baseline is indicative of a moving average of the HRV data during a first number of days, and the HRV baseline is determined based on: a time window T per day, the first number of days, and the HRV-related metric, and the SWC is indicative of a value range for the HRV-related metrics during a second number of days, wherein the SWC is determined based on: a standard deviation of the HRV-related metric during the second number of days, the second number of days, and the HRV-related metric, wherein the second number of days is more than the first number of days.

2. The method of claim 1, wherein the at least one acute stressor is determined using a causal inference engine, and using the causal inference engine comprises using a directed acyclic graph (DAG) to determine statistical dependencies between a first node representing a causally related lifestyle event and a second node representing the HRV event, wherein an edge is established from the first node to the second node upon determining that the causally related lifestyle event associated with the first node is likely to have caused the HRV event associated with the second node, wherein a weight of the edge indicates a conditional probability for the HRV event occurring based on occurrence of the causally related lifestyle event.

3. The method of claim 2, wherein the at least one acute stressor as the probable cause of the HRV event is selected from a plurality of causally related lifestyle events, wherein each of the plurality of causally related lifestyle events is associated with a respective edge to the HRV event on the DAG.

4. The method of claim 1, wherein the HRV-related metric comprises a root mean square of successive time differences (RMSSD) of consecutive heartbeats in a logarithm form.

5. The method of claim 1, wherein the HRV data further comprises a daily HRV score, and the HRV event indicative of the maladaptation risk of the individual is determined to have occurred when the daily HRV score is outside of the value range of the SWC, and the HRV baseline is decreasing.

6. The method of claim 1, wherein the lifestyle events comprise at least one of exercise events or sleep events for the individual.

7. The method of claim 1, wherein the maladaptation risk is associated with a state of the individual indicative of at least one of: inability to respond to the at least one acute stressor, poor adaptation to work, or non-functional overreaching.

8. The method of claim 1, wherein the HRV data further comprises a coefficient of variation (CV), the CV is indicative of a value for assessing adaptation over time to a fitness program or a lifestyle change by the individual, the CV is determined based on: a standard deviation of the HRV-related metric during a third number of days, the third number of days, and the HRV-related metric, wherein the HRV event indicative of the maladaptation risk of the individual is determined to have occurred when the baseline HRV is decreasing and the CV is increasing.

9. The method of claim 1, wherein the environmental contexts associated with the at least one lifestyle event comprise at least one of: information extracted from workout data derived from the sensor data of the device, or at least one of exercise type, duration, timestamp, or space associated with the at least one lifestyle event.

10. The method of claim 1, wherein the at least one acute stressor is associated with at least one lifestyle event of the individual as follows: lower than normal sleep duration, higher than normal workout, decreasing sleep duration, or higher than normal training load.

11. An apparatus for acute stressors detection, comprising:

a non-transitory memory;

a heart rate sensor comprising an inward facing heart rate sensor facing toward or in contact with an individual's skin when the apparatus is worn by the individual; and a processor, wherein the non-transitory memory includes instructions executable by the processor to:

obtain heart rate data collected by the heart rate sensor when the apparatus is worn by the individual;

determine heart rate variability (HRV) data based on an HRV-related metric associated with the individual, wherein the HRV-related metric is derived from the heart rate data;

determine, based on the HRV data, whether an HRV event indicative of a maladaptation risk of the individual has occurred, wherein the HRV event indicative of the maladaptation risk is determined according to at least two different parameters from the HRV data, a first one of the at least two different parameters is derived from the HRV-related metric over time; and responsive to determining that the HRV event indicative of the maladaptation risk of the individual has occurred, determine at least one acute stressor as a probable cause of the HRV event using causal inference techniques based on the HRV event, at least one lifestyle event performed by the individual, and environmental contexts associated with the at least one lifestyle event, wherein the at least one acute stressor is determined by comparing statistical dependencies between the HRV event and each of the at least one lifestyle event, wherein the at least one lifestyle event and the environmental contexts are extracted from sensor data collected by the apparatus, and the sensor data comprises the heart rate data and at least one other type of sensor data collected by the apparatus, wherein the HRV data further comprises an HRV baseline and a smallest worthwhile change (SWC), the HRV baseline is indicative of a moving average of the HRV data during a first number of days, and the HRV baseline is determined based on: a time window T per day, the first number of days, and the HRV-related metric, and the SWC is indicative of a value range for the HRV-related metrics during a second number of days, wherein the SWC is determined based on: a standard deviation of the HRV-related metric during the second number of days, the second number of days, and the HRV-related metric, wherein the second number of days is more than the first number of days.

12. The apparatus of claim 11, wherein the at least one acute stressor is determined using a causal inference engine, and using the causal inference engine comprises using a directed acyclic graph (DAG) to determine statistical dependencies between a first node representing a causally related lifestyle event and a second node representing the HRV event, wherein an edge is established between the first node and the second node upon determining that the causally related lifestyle event associated with the first node is likely to have caused the HRV event associated with the second node, wherein a weight of the edge indicates a conditional probability for the HRV event occurring based on occurrence of the causally related lifestyle event.

13. The apparatus of claim 12, wherein the at least one acute stressor as the probable cause of the HRV event is selected from a plurality of causally related lifestyle events, wherein each of the plurality of causally related lifestyle events is associated with a respective edge to the HRV event on the DAG.

14. The apparatus of claim 11, wherein the HRV-related metric comprises a root mean square of successive time differences (RMSSD) of consecutive heartbeats in a logarithm form.

15. The apparatus of claim 11, wherein the HRV data further comprises a daily HRV score, and the HRV event indicative of the maladaptation risk of the individual is determined to have occurred when the daily HRV score is outside of the value range of the SWC, and the HRV baseline is decreasing.

16. The apparatus of claim 11, wherein the lifestyle events comprise at least one of exercise events or sleep events for the individual, and the environmental contexts associated with the at least one lifestyle event comprise at least one of: information extracted from workout data derived from the sensor data of the apparatus, or at least one of exercise type, duration, timestamp, or space associated with the at least one lifestyle event.

17. The apparatus of claim 11, wherein the maladaptation risk is associated with a state of the individual indicative of at least one of: inability to respond to the at least one acute stressor, poor adaptation to work, or non-functional over-reaching, and the at least one acute stressor is associated with at least one lifestyle event of the individual as follows: lower than normal sleep duration, higher than normal workout, decreasing sleep duration, or higher than normal training load.

18. The apparatus of claim 11, wherein the HRV data further comprises a coefficient of variation (CV), the CV is indicative of a value for assessing adaptation over time to a fitness program or a lifestyle change by the individual, the CV is determined based on: a standard deviation of the HRV-related metric during a third number of days, the third number of days, and the HRV-related metric, wherein the HRV event indicative of the maladaptation risk of the individual is determined to have occurred when the baseline HRV is decreasing and the CV is increasing.

19. A non-transitory computer-readable storage medium configured to store computer programs for acute stressors detection, the computer programs comprising instructions executable by a processor to perform the method of claim 1.

20. The non-transitory computer-readable storage medium of claim 19, wherein the at least one acute stressor is determined using a causal inference engine, and using the causal inference engine comprises using a directed acyclic graph (DAG) to determine statistical dependencies between a first node representing a causally related lifestyle event and a second node representing the HRV event, wherein an edge is established from the first node to the second node upon determining that the causally related lifestyle event associated with the first node is likely to have caused the HRV event associated with the second node, wherein a weight of the edge indicates a conditional probability for the HRV event occurring based on occurrence of the causally related lifestyle event.

* * * * *